United States Patent
Wolfe et al.

(10) Patent No.: US 7,091,183 B1
(45) Date of Patent: *Aug. 15, 2006

(54) SPECIFIC ANTAGONISTS FOR GLUCOSE-DEPENDENT INSULINOTROPIC POLYPEPTIDE (GIP)

(75) Inventors: M. Michael Wolfe, Newton, MA (US); Chi-Chuan Tseng, Newton, MA (US); Linda Neville, Hull, MA (US)

(73) Assignee: Boston Medical Center Corporation, Boston, MA (US)

( * ) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 0 days.

(21) Appl. No.: 08/984,476

(22) Filed: Dec. 3, 1997

Related U.S. Application Data

(60) Provisional application No. 60/032,329, filed on Dec. 3, 1996.

(51) Int. Cl.
   *A61K 38/22* (2006.01)
   *C07K 14/575* (2006.01)

(52) U.S. Cl. .......................... 514/13; 530/326

(58) Field of Classification Search ............. 424/198.1, 424/484, 439; 514/14, 13, 18, 15; 530/325, 530/326
   See application file for complete search history.

(56) References Cited

OTHER PUBLICATIONS

Ngo et al., in The Protein Folding Problem and Tertiary Structure Prediction, Merz and Le Grand (Eds), Aug. 1994, Springer Verlag, pp. 433 and 492-495, Aug. 1994.*
Marx J. Obesity gene discovery may help solve weighty problem [news]. SCIENCE, (Dec. 2, 1994) 266 (5190) 1477-8.*
Woods et al., Signals that regulate food intake and energy homeostasis. Science, 280:1378-1383, May, 29, 1998.*
Gelling et al. (GIP(6-30amide) contains the high affinity binding region of GIP and is a potent inhibitor of GIP1-42 action in vitro. Regul Pept Apr. 30, 1997;69(3):151-4.*
Ebert et al. Influence of gastric inhibitory polypeptide antiserum on glucose-induced insulin secretion in rats. Endocrinology, (Nov. 1982) 111 (5) 1601-6.*
Avis, K.E. "Parenteral Preparations", Chapter 84, in, Remington's Pharmaceutical Sciences, 18th edition (Jun. 1990), Mack Pub. Co., Easton, Pennsylvania, p. 1565.*
Turco, S.J. "Intravenous Admixtures", Chapter 85, in, Remington's Pharmaceutical Sciences, 18th edition (Jun. 1990), Mack Pub. Co., Easton, Pennsylvania, p. 1570.*
Moody et al. The isolation and sequencing of human gastric inhibitory peptide (GIP). FEBS Lett. Jul. 9, 1984;172(2):142-8.*
Deciphering the Message in Protein Sequences: Tolerance to Amino Acid Substitutions, James U. Bowie, et al., Science, vol. 247.

* cited by examiner

*Primary Examiner*—David Romeo
(74) *Attorney, Agent, or Firm*—Edwards Angell Palmer & Dodge LLC; Peter J. Manso

(57) ABSTRACT

In one embodiment, this invention provides an antagonist of glucose-dependent insulinotropic polypeptide (GIP) consisting essentially of a 24 amino acid polypeptide corresponding to positions 7–30 of the sequence of GIP. In another embodiment, this invention provides a method of preventing and treating obesity and non-insulin dependent diabetes mellitus (Type II) in a patient comprising administering to the patient an antagonist of glucose-dependent insulinotropic polypeptide (GIP). In yet another embodiment, this invention provides a method of improving glucose tolerance in a mammal comprising administering to the mammal an antagonist of glucose-dependent insulinotropic polypeptide (GIP).

10 Claims, 6 Drawing Sheets

SPECIFIC ANTAGONISTS FOR GLUCOSE-DEPENDENT INSULINOTROPIC POLYPEPTIDE (GIP)

This application for U.S. Patent claims benefit from U.S. Provisional Application No. 60/032,329, filed on Dec. 3, 1996.

FIELD OF THE INVENTION

This invention is directed to specific antagonists of glucose-dependent insulinotropic polypeptide (GIP). This invention is also directed to treatment of non-insulin dependent diabetes through increasing or improving glucose tolerance without requirement for increased serum insulin, the treatment of obesity by the administration of a GIP antagonist, the development of nonpeptide GIP antagonist compounds, and compositions.

BACKGROUND

Insulin release induced by the ingestion of glucose and other nutrients is due in part to both hormonal and neural factors (Creutzfeldt, et al., 1985, *Diabetologia* 28: 565–573). Several gastrointestinal regulatory peptides have been proposed as incretins, the substance(s) believed to mediate the enteroinsular axis and that may play a physiological role in maintaining glucose homeostasis (Unger, et al., 1969, *Arch. Intern. Med,* 123:261–266; Ebert, R., et al. 1987, *Diab. Metab. Rev.*, 3:1–16; Dupré J., 1991, "The Endocrine Pancreas." Raven Press, New York, p 253). Among these candidates, only glucose-dependent insulinotropic polypeptide (GIP) and glucagon like peptide-1 (7–36) (GLP-1) appear to fulfill the requirements to be considered physiological stimulants of postprandial insulin release (Dupré, et al. 1973, *J. Clin. Endocrinol. Metab.*, 37:826–828; Nauck, et al., 1989, *J. Clin. Endocrinol. Metab.*, 69:6540662; Kreymann, et al. 1987, *Lancet*, 2:1300–1304; Mojsov, et al., 1987, *J. Clin. Invest.*, 79:616–619).

Following oral glucose administration, serum GIP levels increase several fold (see Cleator, et al., 1975, *Am. J. Surg.*, 130:128–135; Nauck, et al. 1986, *J. Clin. Endocrinol. Metab.*, 63:492–498; Nauck, et al., 1986, *Diabetologia*, 29:46–52; Salera, et al., 1983, *Metabolism*, 32:21–24; Kreymann, et al., 1987, *Lancet*, 2:1300–1304), and although the increment in plasma GLP-1 concentration in response to glucose is also significant, it is far smaller in magnitude (Kreymann, et al., 1987, *Lancet*, 2:1300–1304; Ørskov, et al., 1987, *Scand. J. Clin. Invest.*, 47:165–174; Ørskov, et al., 1991, *J. Clin. Invest.*, 87: 415–423; Shuster, et al., 1988, *Mayo Clin. Proc.*, 63:794–800). In human volunteers, Nauck et al. (1993, *J. Clin. Endocrinol. Metab.*, 76:912–917) showed that GIP and GLP-1 are major contributors in the incretin effect after oral glucose. Shuster et al. (1988) also suggested that GIP was the most important, but not the sole, mediator of the incretin effect in humans.

Some studies have demonstrated that GIP and GLP-1 are equally potent in their capacity to stimulate insulin release (Schmid, et al., 1990, *Z. Gastroenterol.*, 28:280–284; Suzuki, et al., 1990, *Diabetes*, 39:1320–1325), whereas others have suggested that GLP-1 possesses greater insulinotropic properties (Siegel, et al. 1992, *Eur. J. Clin. Invest.* 22:154–157; Shima, et al. 1988, *Regul. Pept.*, 22:245–252). Recently, using a putative specific antagonist to the GLP-1 receptor, exendin (9–39), Wang et al. have demonstrated that exendin reduced postprandial insulin release by 48% and thus concluded that GLP-1 might contribute substantially to postprandial stimulation of insulin secretion (Wang, et al. 1995, *J. Clin. Invest.*, 95:417–421). More recent studies, however, have shown that exendin might also displace GIP binding from its receptor and thereby reduce GIP-stimulated cyclic adenosine monophosphate (cAMP) generation (Wheeler, et al. 1995, *Endocrinology*, 136:4629–4639; Gremlich, et al. 1995, Diabetes, 44:1202–1208). Therefore, the antagonist properties of exendin (9–39) might not be limited to GLP-1.

The availability of a GIP-specific receptor antagonist would be invaluable for determining the precise roles of these peptides in mediating postprandial insulin secretion.

SUMMARY OF THE INVENTION

It is an object of this invention to provide specific antagonists of glucose-dependent insulinotropic polypeptide (GIP).

It is another object of this invention to provide alternative methods for treatment of non-insulin dependent diabetes (Type II) with increased or improved glucose tolerance without requirement for increased serum insulin, for treatment of obesity with a GIP antagonist which inhibits, blocks or reduces glucose absorption from the intestine of an animal, and for development of nonpeptide GIP antagonist compounds.

In one embodiment, this invention provides an antagonist of glucose-dependent insulinotropic polypeptide (GIP) consisting essentially of a 24-amino acid polypeptide corresponding to positions 7–30 of the sequence of GIP (SEQ ID NO:2 and SEQ ID NO:8).

In another embodiment, this invention provides a method of treating non-insulin dependent diabetes mellitus in a patient comprising administering to the patient an antagonist of glucose-dependent insulinotrophic polypeptide (GIP).

In yet another embodiment, this invention provides a method of improving glucose tolerance in a mammal comprising administering to the mammal an antagonist of glucose-dependent insulinotropic polypeptide (GIP).

Using a reporter L-cell line stably transfected with rat GIP receptor cDNA (LGIPR2), the inventors have identified a fragment of GIP [GIP (7–30)-$NH_2$] (SEQ ID NO:2 and SEQ ID NO:8) as a specific GIP receptor antagonist (SEQ ID NO:2 and SEQ ID NO:8). This antagonist (referred to as ANTGIP (SEQ ID NO:8)) inhibited GIP-stimulated intracellular cAMP production in vitro, and ANTGIP (SEQ ID NO:8) competed with GIP for binding to cellular receptors, but did not complete with GLP-1. ANTGIP (SEQ ID NO:8) inhibited the GIP-dependent release of insulin in vivo, but ANTGIP (SEQ ID NO:8) had no effect on glucose-, GLP-1-, GIP-, and arginine-induced insulin release in anesthetized rats. In conscious rats, ANTGIP (SEQ ID NO:8) inhibited postprandial insulin release, without significantly affecting the serum glucose concentration. However, despite its inhibiting effect on insulin release, ANTGIP (SEQ ID NO:8) has been discovered to enhance glucose tolerance in an oral glucose tolerance test.

DETAILED DESCRIPTION OF THE INVENTION

Figure 1A:
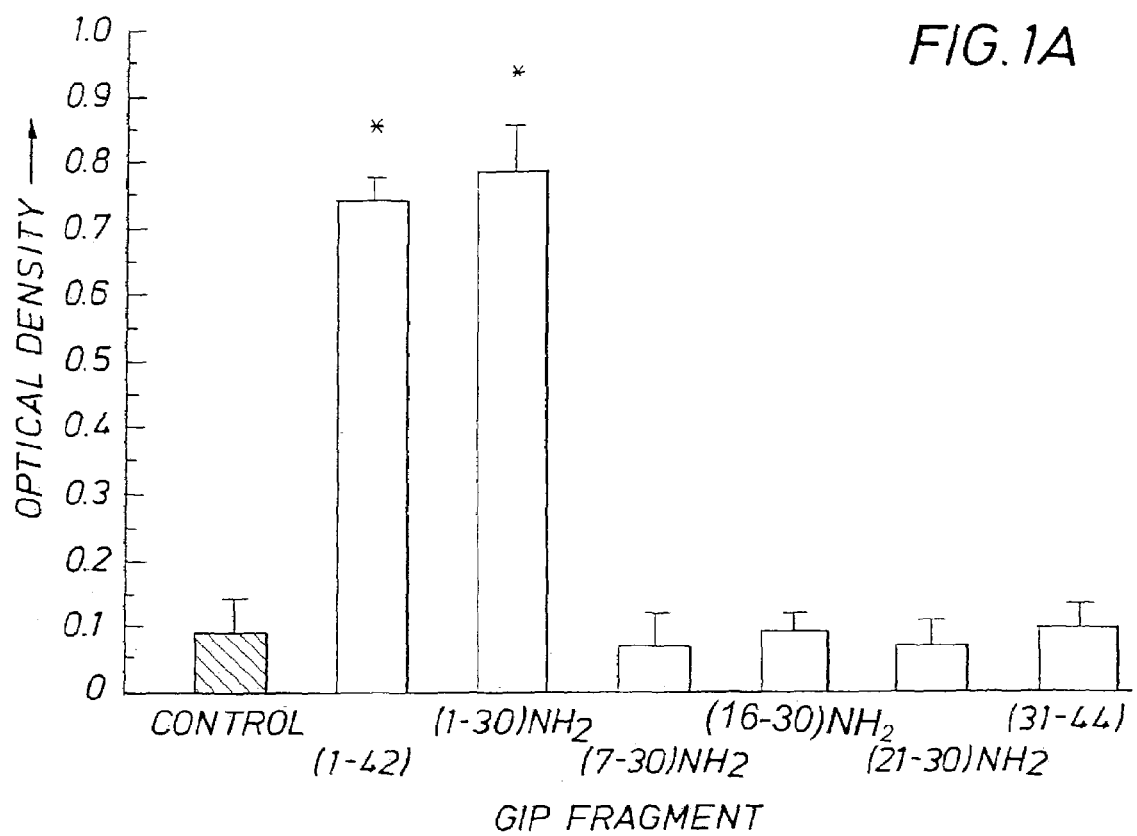
FIGS. 1A and 1B show cAMP-dependent β-galactosidase production by LGIPR2 cells in the presence of GIP or various GIP fragments.

Glucose-dependent insulinotropic polypeptide (GIP) is a 42-amino acid hormone (SEQ ID NO:11 and SEQ ID NO:12) that was originally described as an inhibitor of acid secretion. More recently, however, it has been shown to be potent stimulant for the release of insulin from the endocrine pancreas.

The inventors have confirmed previous studies (Rossowski, et al., 1992, *Regul. Pep.*, 39:9–17) indicating that truncated GIP [GIP (1–30)-NH$_2$] (SEQ ID NO:1 and SEQ ID NO:7) might be one of the biologically active forms of mature GIP. As shown in FIG. 1, GIP (1–30)-NH$_2$ (SEQ ID NO:1 and SEQ ID NO:7) was nearly equipotent to GIP (1–42) (SEQ ID NO:11 and SEQ ID NO:12) in stimulating cAMP dependent β-galactosidase production in LGIPR2 cells. These findings are consistent with the observations of Wheeler, et al. (1995), which reported that both GIP(1–42) (SEQ ID NO:11 and SEQ ID NO:12) and GIP (1–30) (SEQ ID NO:1 and SEQ ID NO:7) exhibited similar stimulatory properties for cAMP production in COS-7 cell transiently expressing GIP receptor cDNA. Moreover, Kieffer et al. (1993, *Can. J. Physiol. Pharmacol.*, 71:917–922) found that GIP (1–30) (SEQ ID NO:1 and SEQ ID NO:7) competitively inhibited binding of GIP (1–42) (SEQ ID NO:11 and SEQ ID NO:12) to the GIP receptor in βTC3 cells. These data suggest the possibility of cellular processing of GIP (1–42) (SEQ ID NO:11 and SEQ ID NO:12) to yield biologically-active α-amidated GIP (1–30) (SEQ ID NO:1 and SEQ ID NO:7).

Physiological Effects of GIP Antagonists

Insulin release induced by the ingestion of glucose and other nutrients is due in part to both hormonal and neural factors (see, e.g., Creutzfeldt, et al., 1985). Although a number of gastrointestinal regulatory peptides have been proposed as putative incretins, GIP and GLP-1 are the most likely physiological insulinotropic peptides. Although both GIP and GLP-1 possess significant insulinotropic properties, controversy exists regarding their relative physiological roles in stimulating insulin release.

Using a GLP-1 receptor antagonist exendin (9–39), Wang et al. (1995) detected a 50% decrease in postprandial insulin secretion in exendin-treated rats. Administration of exendin also reduced 70% of insulin release following intraduodenal glucose infusion (Kolligs, et al., 1995, *Diabetes*, 44:16–19). Recent studies, however, have demonstrated that exendin also displaced GIP binding from its receptor, and inhibits cAMP generation in response to GIP stimulation (Wheeler, et al. 1995; Gremlich, et al. 1995). Therefore, the antagonist properties of exendin do not appear to be GLP-1 specific.

Successful synthesis by the present inventors of a specific GIP receptor antagonist greatly facilitates investigation of the relative contribution of GIP in mediating the enteroinsular axis. The GIP fragment ANTGIP (SEQ ID NO:8) [GIP (7–30)-NH$_2$] (SEQ ID NO:2 and SEQ ID NO:8) specifically inhibits various GIP-dependent effects. In LGIPR2 cells, ANTGIP (SEQ ID NO:8) inhibited the cAMP response to GIP in a concentration-dependent manner (see FIG. 2), and in βTC3 cells, the antagonist displaced GIP binding from its receptor (see FIG. 3). Furthermore, ANTGIP (SEQ ID NO:8) completely abolished the insulinotropic properties of GIP in fasted anesthetized rats, while not affecting GLP-1, glucose-, or arginine-stimulated insulin release indicating that this antagonist is GIP-specific. ANTGIP (SEQ ID NO:8) alone demonstrated no stimulatory effect on insulin release or cAMP generation in either intact rats or LGIPR2 cells, indicating the absence of any agonist properties. Studies demonstrated that even at a concentration as high as $10^{-4}$ M, ANTGIP (SEQ ID NO:8) did not stimulate a detectable increase in cAMP-dependent β-galactosidase level in LGIPR2 cells.

The inventors have observed a 72% decrease in postprandial insulin release in response to the administration of ANTGIP (SEQ ID NO:8) to rats. ANTGIP (SEQ ID NO:8) did not affect GLP-1 binding to its receptor, and the insulinotropic effect of GLP-I is preserved in vivo in the presence of ANTGIP (SEQ ID NO:8). Furthermore, postprandial GLP-1 levels were not affected by ANTGIP (SEQ ID NO:8). These findings are consistent with a dominant role for GIP in mediating the enteroinsular axis.

Wang et al. demonstrated an approximate 50% reduction in postprandial insulin levels in exendin-treated rats, wherein plasma glucose levels increased minimally from 7.5 to 8.7 mmol/l. The physiological significance of this minor increment in glucose level was not clear to Wang, et al. The inventors found that serum glucose concentrations remained largely unchanged despite a marked decrease in serum insulin levels in ANTGIP (SEQ ID NO:8)-treated rats. The results of the present study are consistent with the notion that insulin is not the sole mediator of glucose homeostasis, but that glucose maintenance is dependent on numerous neurohumoral factors. These factors include hormones, such as pancreatic glucagon, cortisol, and growth hormone, and physiological events, including peripheral and hepatic glucose uptake.

The results of the present studies demonstrate that GIP (7–30)-NH$_2$ (SEQ ID NO:2 and SEQ ID NO:8) is a specific receptor antagonist of naturally occurring GIP. GIP (7–30)-NH$_2$ (SEQ ID NO:2 and SEQ ID NO:8) inhibits GIP-induced cAMP generation and insulin release, but does not affect the insulinotropic effects of other secretagogues such as glucose, arginine and GLP-1. Furthermore, circulating insulin levels decreased by 72% in response to the concomitant administration of GIP (7–30)-NH$_2$ (SEQ ID NO:2 and SEQ ID NO:8) to chow-fed rats, indicating that GIP plays a dominant role in mediating postprandial insulin secretion.

Strikingly, although GIP (7–30)-NH$_2$ (SEQ ID NO:2 and SEQ ID NO:8) reverses the insulin stimulatory properties of the parent compound, when the GIP antagonist was administered to rats (injected intraperitoneally), oral glucose tolerance was improved: a significant decrease in serum glucose levels was detected at all time points in all rats. In addition, plasma insulin levels were also diminished in these same rats. The results are surprising—with the decrease in insulin release, one would expect an increase in serum glucose. However, GIP has several other peripheral effects which may include an affect of GIP on peripheral glucose utilization, and the decrease in serum glucose levels seen with GIP might be due to such an effect.

The effect of GIP antagonists on serum glucose levels in the absence of increased serum insulin suggests their use in patients with noninsulin dependent diabetes mellitus (NIDDM). With the aging of the United States population, an increase in the number of cases of NIDDM has been predicted. In the past forty years, very few new forms of therapy for this most prevalent disease have been developed. GIP antagonists enhance tolerance to oral glucose, as demonstrated herein, and therefore treatment of NIDDM patients with these compounds is indicated.

GIP Antagonists

A GIP antagonist according to this invention is any composition which interferes with biological action of GIP. Such compositions include antibodies specific for either GIP or GIP receptors, antisense RNA which hybridizes with mRNA encoding GIP or GIP receptor, or other genetic controls which knock out expression of GIP or GIP receptor. GIP antagonists also include peptides or other small molecules which bind to the GIP receptor and block the cAMP response to GIP. Suitable assays for antagonist activity are exemplified in Examples 1 and 2 below:

As described herein (see Example 1 below), the inventors have now discovered a polypeptide fragment of GIP that is a specific GIP receptor antagonist. While the 30-amino acid N-terminal fragment [GIP (1–30)-NH$_2$] (SEQ ID NO:1 and SEQ ID NO:7) was as effective in stimulating cAMP increase through GIP receptors as the parent hormone, a fragment missing the most N-terminal six amino acids [GIP (7–30)-NH$_2$] (SEQ ID NO:2 and SEQ ID NO:8) did not stimulate cAMP release in the same system. Thus, the N-terminal hexamer appears to be important for functional GIP signaling. GIP fragments missing the N-terminal 15 amino acids (e.g., GIP (16–30)-NH$_2$) (SEQ ID:3 and SEQ ID NO:9) did not mimic GIP, but neither did they inhibit GIP-dependent effects. Thus, the segment from amino acids 7–15 (SEQ ID NO:4) appears to be especially important in signaling through the GIP receptor. Fragment GIP (10–30)-NH$_2$ (SEQ ID NO:5 and SEQ ID NO:10) was less effective as an antagonist, but retained some ability to affect GIP receptor activation, as indicated by partial agonist activity. Thus, peptide antagonists would appear to require the segment from amino acids 7–9 (SEQ ID NO:6) of the GIP sequence, and some or all of the amino acids from 10–30 (SEQ ID NO:5 and SEQ ID NO:10) or effective alternative amino acids thereto are likely to promote binding to the receptor.

It should therefore be understood by those of skill in this art that the present invention contemplates any polypeptide sequence which effectively prevents GIP activation of its native receptor, such as the sequence containing amino acids in positions 7–30 of the sequence of GIP sequence (SEQ ID NO:2 and SEQ ID NO:8) and polypeptides based upon sequences containing amino acids in positions 7–30 of the sequence of the GIP (SEQ ID NO:2 and SEQ ID NO:8) that include additional, deleted or alternative amino acids to form an effective GIP polypeptide antagonist. Polypeptides based on this sequence may be designed for use as GIP antagonists according to this invention by the skilled artisan, who will routinely confirm that the resultant peptides exhibit antagonist function by testing the peptides in in vitro and in vivo assays such as those described in Examples 1 and 3–5 below.

Immunologic components specific for GIP or GIP receptors can be employed as GIP antagonists. Such antagonists include specific monoclonal antibodies (either naked or conjugated to cytotoxic agents) or specific activated cytotoxic immune cells. Such antibodies or immune cells may be generated as reagents outside the body, or may be generated inside the body by vaccines which target GIP or GIP receptors.

Antibodies which are specifically reactive with GIP or the hormone binding domain of the GIP receptor, or antigenic recombinant peptide fragments of either of those proteins, may be obtained in a number of ways which will be readily apparent to those skilled in the art. The known sequences of GIP (see Takeda, et al. 1987, *Proc. Natl. Acad. Sci USA,* B84:7005–7008, and Genbank Accession No. M18185), and GIP receptor (see Bonner, T. I., and Usdin, T. B., 1995, Genbank Accession No U39231) can be used in conjunction with standard recombinant DNA technology to produce the desired antigenic peptides in recombinant systems (see, e.g., Sanbrook et al.). Antigenic fragments of GIP or GIP receptor can be injected into an animal as an immunogen to elicit polyclonal antibody production. Purification of the antibodies can be accomplished by selective binding from the serum, for instance by using cells transformed with DNA sequence encoding the respective proteins. The resultant polyclonal antisera may be used directly or may be purified by, for example, affinity absorption using recombinantly produced protein coupled to an insoluble support.

In another alternative, monoclonal antibodies specifically immunoreactive with either GIP or the hormone binding domain of GIP receptor may be prepared according to well known methods (See, e.g., Kohler and Milstein, 1976, *Eur. J. Immunol.,* 6:611), using the proteins or antigenic fragments described above as immunogen(s), using them for selection or using them for both functions. These and other methods for preparing antibodies or immune cells that are specifically immunoreactive with GIP or GIP receptor are easily within the skill of the ordinary worker in the art.

Immunogenic compositions according to this invention for use in active immunotherapy include recombinant antigenic fragments of GIP or GIP receptor prepared as described above and expression vectors (particularly recombinant viral vectors) which express antigenic fragments of GIP or GIP receptor. Such expression vectors can be prepared as described in Baschang, et al., U.S. Pat. No. 4,446,128, incorporated herein by reference, or Axel, et al., Pastan, et al., or Davis, et al., using the known sequences of GIP or GIP receptor.

Still another GIP antagonist according to this invention is an expression vector containing an antisense sequence corresponding to all or part of an mRNA sequence encoding GIP or GIP receptor, inserted in opposite orientation into the vector after a promoter. As a result, the inserted DNA will be transcribed to produce an RNA which is complementary to and capable of binding or hybridizing to the mRNA. Upon binding to the GIP or GIP receptor mRNA, translation of the mRNA is prevented, and consequently the protein coded for by the mRNA is not produced. Suitable antisense sequences can be readily selected by the skilled artisan from the sequences of GIP or GIP receptor cited above. Production and use of antisense expression vectors is described in more detail in U.S. Pat. No. 5,107,065 and U.S. Pat. No. 5,190,931, both of which are incorporated herein by reference.

Alternative materials within the contemplation of the skilled artisan which function as antagonists of GIP in the procedures described in Examples 1 and 3–5 below may also be used in the therapeutic methods according to this invention.

Therapeutic use of GIP Antagonists

GIP (7–30)-NH$_2$ (SEQ ID NO:2 and SEQ ID NO:8) acts as a receptor antagonist of GIP, but also improves glucose tolerance contrary to the expected consequence of blocking GIP-dependent insulin secretion. In addition, a GIP receptor antagonist in accordance with the present invention inhibits, blocks or reduces glucose absorption from the intestine of an animal. In accordance with this observation, therapeutic compositions containing GIP antagonists may be used in patients with noninsulin dependent diabetes mellitus (NIDDM) to improve tolerance to oral glucose or in animals, such as humans, to prevent, inhibit or reduce obesity by inhibiting, blocking or reducing glucose absorption from the intestine of the animal, as demonstrated herein.

Therapeutic compositions according to this invention are preferably formulated in pharmaceutical compositions containing one or more GIP antagonists and a pharmaceutically acceptable carrier. The pharmaceutical composition may contain other components so long as the other components do not reduce the effectiveness of the GIP antagonist according to this invention so much that the therapy is negated. Examples of such components included sweetening, flavoring, coloring, dispersing, disintegrating, binding, granulating, suspending, wetting, preservative and demulcent agents and the like. Pharmaceutically acceptable carriers are well known, and one skilled in the pharmaceutical art can easily select carriers suitable for particular routes for administration (*Remington's Pharmaceutical Sciences*, Mack Publishing Co., Easton, Pa., 1985).

Also in accordance with the present invention, the GIP receptor antagonist of the present invention may be lyophilized using standard techniques known to those in this art. The lyophilized GIP receptor antagonists may then be reconstituted with, for example, suitable diluents such as normal saline, sterile water, glacial acetic acid, sodium acetate, combinations thereof and the like. The reconstituted GIP receptor antagonists in accordance with the present invention may be administered parenterally or orally and may further include preservatives or other acceptable inert components as mentioned hereinbefore.

The pharmaceutical compositions containing any of the GIP antagonists according to this invention may be administered by parenteral (subcutaneously, intramuscularly, intravenously, intraperitoneally, intrapleurally, intravesicularly or intrathecally), topical, oral, rectal, inhalation or nasal route, as necessitated by choice of drug and disease. The dose used in a particular formulation or application will be determined by the requirements of the particular state of disease and the constraints imposed by the characteristics of capacities of the carrier materials. The concentrations of the active agent in pharmaceutically acceptable carriers may range from 0.1 nM to 100 μM. The compositions described above may be combined or used together or in coordination with another therapeutic substance.

Dose will depend on a variety of factors, including the therapeutic index of the drugs, disease type, patient age, patient weight, and tolerance of toxicity. Dose will generally be chosen to achieve serum concentrations from about 0.1 μg/ml to about 100 μg/ml. Preferably, initial dose levels will be selected based on their ability to achieve ambient concentrations shown to be effective in in-vitro models, such as that used to determine therapeutic index, and in-vivo models and in clinical trials, up to maximum tolerated levels. Standard clinical procedure prefers that chemotherapy be tailored to the individual patient and the systemic concentration of the chemotherapeutic agent be monitored regularly. The dose of a particular patient can be determined by the skilled clinician using standard pharmacological approaches in view of the above factors. The response to treatment may be monitored by analysis of blood or body fluid levels of the glucose or GIP or GIP antagonist according to this invention, measurement of activity if the antagonist or its levels in relevant tissues or monitoring disease state of the patient. The skilled clinician will adjust the dose based on the response to treatment revealed by these measurements.

One approach to therapy of NIDDM is to introduce vector expressing antisense sequences to block expression of GIP and/or GIP receptor. In one embodiment of this invention, a method is provided which comprises obtaining a DNA expression vector containing a cDNA sequence having the sequence of human GIP or GIP receptor mRNA which is operably linked to a promoter such that it will be expressed in antisense orientation, and transforming cells which express GIP or GIP receptor, respectively, with the DNA vector. The expression vector material is generally produced by culture of recombinant or transfected cells and formulated in a pharmacologically acceptable solution or suspension, which is usually a physiologically-compatible aqueous solution, or in coated tablets, tablets, capsules, suppositories, inhalation aerosols, or ampules, as described in the art, for example in U.S. Pat. No. 4,446,128, incorporated herein by reference.

The vector-containing composition is administered to a mammal exhibiting NIDDM in an amount sufficient to transect a substantial portion of the target cells of the mammal. Administration may be any suitable route, including oral, rectal, inhalation, intranasal or by intravesicular (e.g. bladder) instillation or injection where injection may be, for example, transdermal, subcutaneous, intramuscular in intravenous. Preferably, the expression vector is administered to the mammal so that the target cells of the mammal are preferentially transfected. Determination of the amount to be administered will involve consideration of infectivity of the vector, transfection efficiency in vitro, immune response of the patient, etc. A typical initial dose for administration would be 10–1000 micrograms when administered intravenously, intramuscularly, subcutaneously, intravesicularly, or in inhalation aerosol, 100 to 1000 micrograms by mouth, $10^5$ to $10^{10}$ plaque forming units of a recombinant vector, although this amount may be adjusted by a clinician doing the administration as commonly occurs in the administration of other pharmacological agents. A single administration may usually be sufficient to produce a therapeutic effect, but multiple administrations may be necessary to assure continued response over a substantial period of time.

Further description of suitable methods of formulation and administration according to this invention may be found in U.S. Pat. Nos. 4,592,002 and 4,920,209, which are incorporated herein by reference in their entireties.

The present invention also contemplates the use of the GIP antagonists and/or its properties to develop nonpeptide compounds which exhibit antagonist properties similar to the GIP polypeptide antagonists as herein described using techniques known those versed in the pharmaceutical industry.

EXAMPLES

In order to facilitate a more complete understanding of the invention, a number of Examples are provided below. However, the scope of the invention is not limited to specific embodiments disclosed in these Examples, which are for purposes of illustration only.

Example 1

Effects of Various Peptide Fragments on cAMP Production

To define the biologically active region of GIP, the effects of several peptide fragments of GIP on stimulating cAMP-dependent β-galactosidase production in LGIPR2 cells were examined. LGIPR2 cells are stably transfected with a cAMP-dependent promoter from the VIP gene fused to the bacterial lac Z gene. When intracellular cAMP increases within these cells, lac Z gene transcription is activated, resulting in the accumulation of its product, β-galactosidase. The measurement of β-galactosidase in this system provided a convenient, inexpensive, and nonradioactive method for detecting changes in the levels of intracellular cAMP.

LGIPR2 cells were grown in Dulbecco's Modified Eagle's Medium (DMEM) containing 4.5 g/L of glucose and 10% fetal calf serum. For each assay, $10^5$ cells/well were seeded onto 24-well plates. After incubation overnight, peptides were added in various concentrations to the wells in the absence of 3-isobutyl-methylxanthine (IBMX) for 4 h, at which time maximal stimulation of β-galactosidase was determined. The medium was then removed and wells rinsed once with phosphate-buffered saline (PBS). The plates were then blotted briefly and frozen overnight at $-70°$ C., and, after the addition of chlorophenol red-β-D-galactopyranoside, accumulated β-galactosidase was detected using a calorimetric assay, as described previously (Usdin, et al., 1993, *Endocrinology*, 133:2861–2870).

Figure 1B:
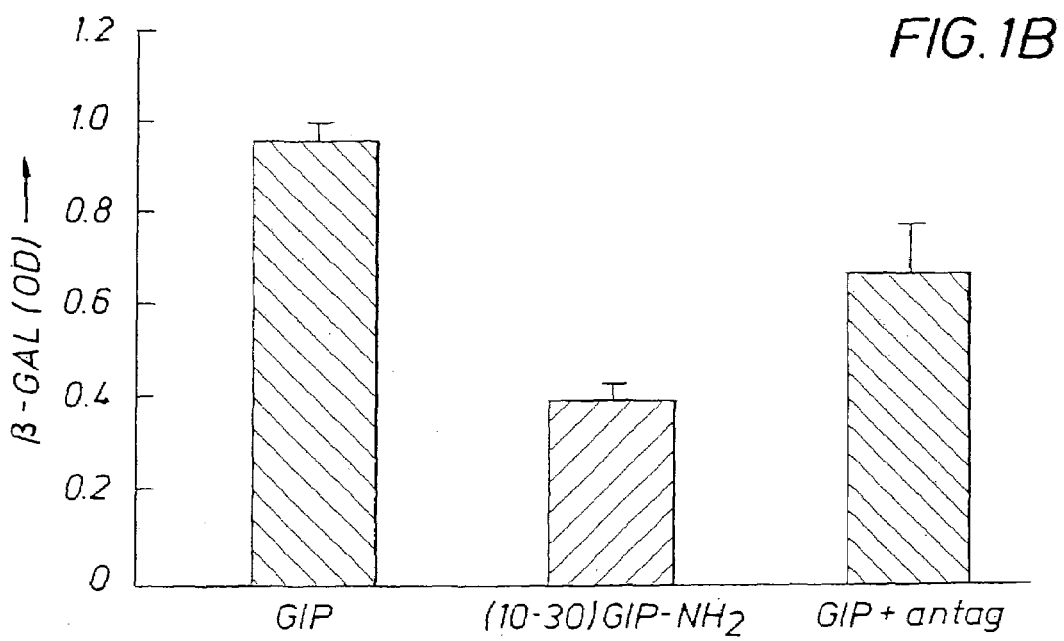

Preliminary studies using LGIPR2 cells demonstrated that GIP (1–42) (SEQ ID NO:12) stimulated β-galactosidase production in a concentration-dependent manner, with the maximum effect observed at 4 h with $10^{-8}$M. Various peptide fragments of GIP, including GIP (21–30)$NH_2$ (SEQ ID:13), GIP (16–30)-$NH_2$ (SEQ ID NO:9), GIP (7–30)-$NH_2$ (SEQ ID NO:8), GIP (1–30)-$NH_2$ (SEQ ID:7), GIP (10–30)-$NH_2$ (SEQ ID: 10), and GIP (31–44) (SEQ ID: 14), were synthesized at the Biopolymer Laboratory, Harvard Medical School, based on previously published rat GIP cDNA sequence (Tseng, et al., 1993, *Proc. Natl. Acad. Sci. USA*, 90:1992–1996). LGIPR2 cells were incubated in the presence of $10^{-8}$ M GIP or different GIP fragments for 4 h, and β-galactosidase was measured as described herein and expressed in optical density (O.D.) units. FIGS. 1A and 1B show cyclic AMP-dependent β-galactosidase generation in LGIPR2 cells in response to incubation with different fragments of GIP. Values are expressed as the mean±SE of quadruplicate measurements (*p<0.01, compared to control).

As demonstrated in FIG. 1A, $10^{-8}$ M GIP (1–30)-$NH_2$ (SEQ ID NO:7) stimulated β-galactosidase production to a similar degree, while none of the other peptide fragments tested, including GIP (7–30)-$NH_2$ (SEQ ID NO:8), GIP (16–30)-$NH_2$ (SEQ ID NO:9), GIP (21–30)-$NH_2$ (SEQ ID NO:13), GIP (31–44) (SEQ ID NO:14), stimulated β-galactosidase generation above control levels. Furthermore, no changes in cAMP-dependent-β-galactosidase levels were detected when LGIPR2 cells were incubated in the presence of higher concentrations of the smaller peptide fragments.

Figure 2:
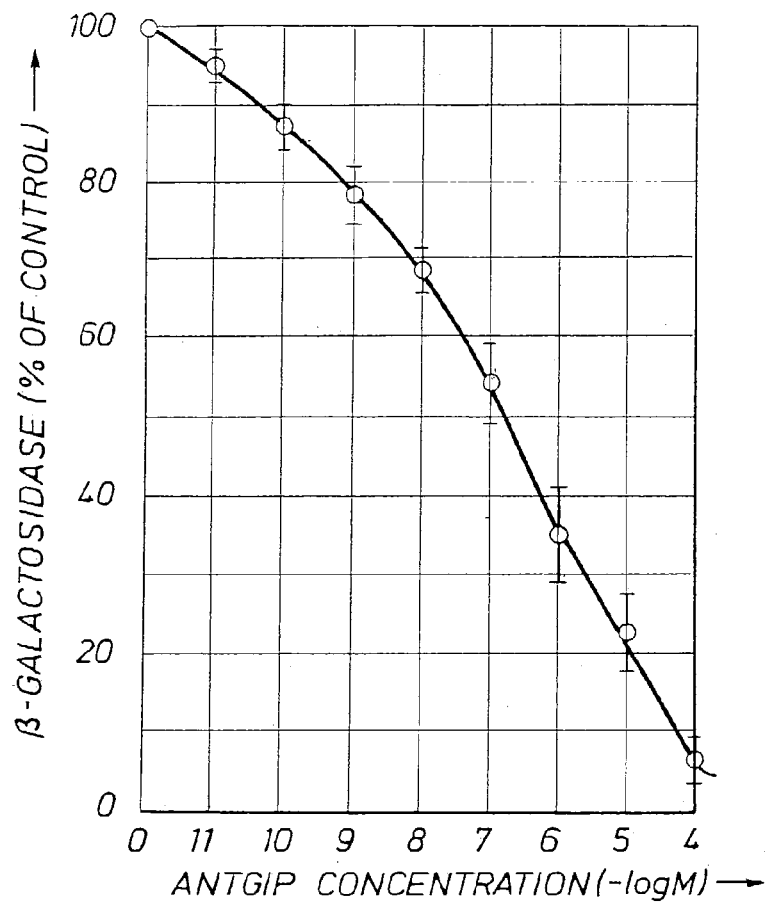
FIG. 2 shows dose-dependent inhibition of ANTGIP (SEQ ID NO:8) on GIP-included cAMP-dependent β-galactosidase production in LGIPR2 cells.

To examine whether any of these fragments might serve as an antagonist to GIP, LGIPR2 cells were incubated with $10^{-8}$ M GIP (1–42) (SEQ ID NO:12) and one of the peptide fragments at two different concentrations ($10^{-8}$ M or $10^{-6}$ M) for 4 h. LGIPR2 cells were cultured in the presence of $10^{-8}$ M GIP and various concentrations of ANTGIP (SEQ ID NO:8), as depicted on the horizontal axis of FIG. 2. Values are expressed as the mean±SE of quadruplicate measurements. Only GIP (7–30)-$NH_2$ (ANTGIP (SEQ ID NO:8)) was found to attenuate the cAMP stimulatory effects exhibited by GIP (1–42) (SEQ ID NO:12); the inhibition was concentration-dependent, with half-maximal inhibition occurring at $10^{-7}$ M (FIG. 2).

FIG. 1B shows that peptide GIP (10–30)-$NH_2$ (SEQ ID NO:10) is an antagonist, albeit a weak one, as demonstrated by the reduction in GIP-stimulated β-gal levels when GIP (10–30)-$NH_2$ (SEQ ID NO:10) is present with GIP (1–42) (SEQ ID NO:12) compared to GIP (1–42) (SEQ ID NO:12) alone. On the other hand, GIP (10–30)-$NH_2$ (SEQ ID NO:10) also has agonist properties, as demonstrated by β-gal level of 0.39 O.D.±0.03 stimulated by GIP (10–30)-$NH_2$ (SEQ ID NO:10) alone, compared to 0.95±0.04 for GIP (1–42) (SEQ ID NO:12).

Example 2

Receptor Binding Studies

Figure 3A:
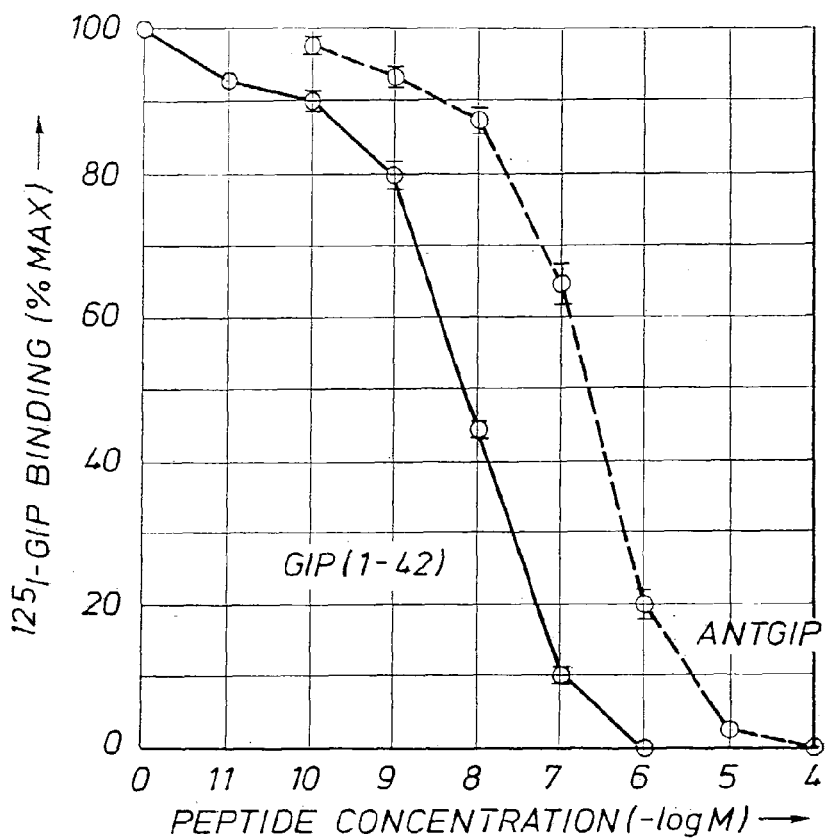
FIG. 3 shows competition of $^{125}$I-GIP and $^{125}$I GLP-I (inset) binding by GIP, GLP-1 and ANTGIP (SEQ ID NO:8).
Figure 3B:
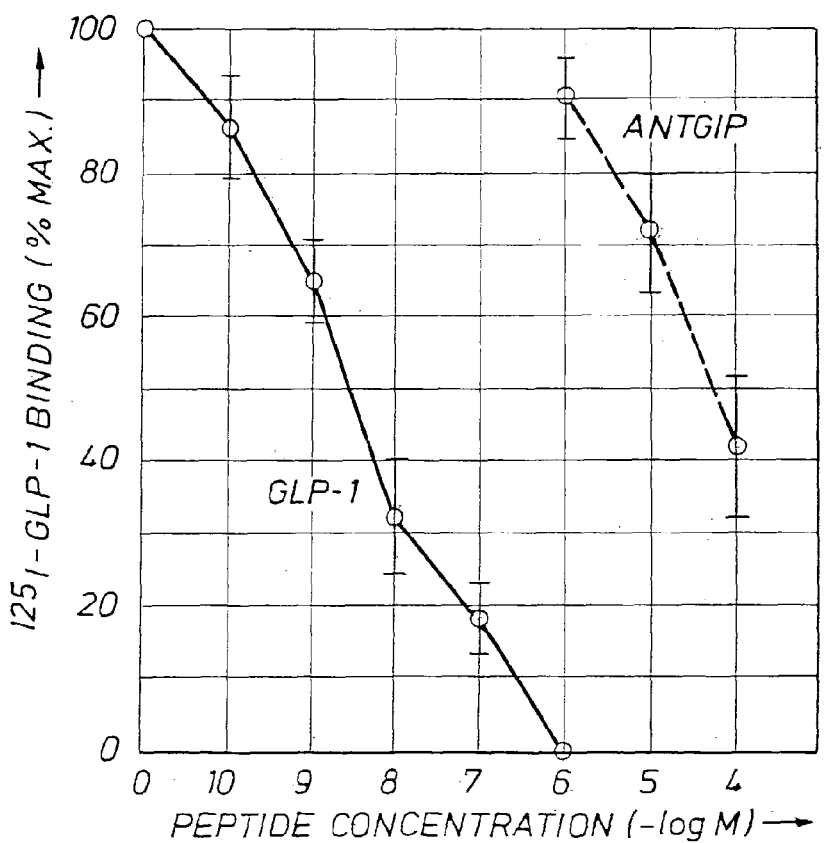

Binding studies were performed in either LGIPR2 or βTC3 cells to determine the relative affinities of GIP, ANTGIP (SEQ ID NO:8), and GLP-1 for both GIP and GLP-1 receptors. GLP (7–37) and porcine GIP (5 μg each) were iodinated by the chloramine-T method and were purified using C-18 cartridges (Sep-Pak®t, Millipore, Milford, Mass.) using an acetonitrile gradient of 30–45%. The specific activity of radiolabeled peptides was 10–50 μCi/mg (Hunter, et al., 1962, *Nature*, 194:495–498; Kieffer, et al., 1993, *Can. J. Physiol. Pharmacol.*, 71:917–922). Aliquots were lyophilized and reconstituted in assay buffer at 4° C. to a concentration of $3\times10^5$ cpm/100 μl. Binding studies was performed in desegrated LGIPR2 or βTC2 cells, the latter a generous gift from Dr. S. Efrat (Diabetes Center, Albert Einstein College of Medicine, New York). The βTC2 cell line originally arose in a lineage of transgenic mice expressing an insulin promoted, SV40 T-antigen hybrid oncogene in pancreatic β-cells (Efrat, et al., 1988, *Proc. Natl. Acad. Sci. U.S.A.*, 85:9037–9041) and has previously been demonstrated to be responsive to both GIP and GLP (Kieffer, et al., 1993, *Can. J. Physiol. Pharmacol.*, 71:917–922). The receptor binding buffer contained 138 mM NaCl, 5.6 mM KCl, 1.2 mM $MgCl_2$, 2.6 mM $CaCl_2$, 10 mM Hepes, 10 mM glucose, and 1% bovine serum albumin (BSA, fraction V, protease free, Sigma). For binding assays, LGIPR2 (GIP binding) or βTC3 (GLP-1 binding) cells were cultured in DMEM containing 4.5 g/L of glucose and 10% fetal bovine serum until 70% confluent. Cells were washed once with PBS and then harvested with PBS-EDTA solution. βTC3 cells were then suspended in assay buffer at a density of $2\times10^6$ cells/ml, and LGIPR2 cells were used at a density of $2.5\times10^5$ cells/ml. Binding was performed at room temperature in the presence of $3\times10^5$ cpm/ml of $[^{125}I]$-GIP and -GLP. Nonsaturable binding was determined by the amount of radioactivity associated with cells when incubated in the presence of unlabeled $10^{-6}$ M GIP, GLP, or $10^{-4}$ M ANTGIP (SEQ ID NO:8). Specific binding was defined as the difference between counts in the absence and presence of unlabeled peptide. GIP binding was examined using LGIRP2 cells, and GLP-1 binding was assessed using βTC3 cells, and the results are shown in FIG. 3. Values are expressed as a percentage of maximum specific binding and are the mean±SE, with assays performed in duplicate.

GIP and ANTGIP (SEQ ID NO:8) displaced the binding of [$^{125}$I]GIP to LGIPR2 cells in a concentration-dependent manner (FIG. 3), with an $IC_{50}$ of 7 nM for GIP (n=5) and 200 nM for ANTGIP (SEQ ID NO:8) (n=4). Binding of [$^{125}$I] GLP-1 to its βTC3 cell receptor was displaced fully by GLP-1, but negligibly by ANTGIP (SEQ ID NO:8), with an $IC_{50}$ of 4 nM and 80 μM, respectively (n=7; FIG. 3).

Example 3

Intravenous Infusion of Peptides in Fasting Anesthetized Rats

Adult male Sprague-Dawley rats (250–350 g) were purchased from Charles River Co. (Kingston, Mass.). For infusion studies, rats were fasted overnight and then anaesthetized using intraperitoneal sodium pentobarbital. The right jugular vein was cannulated with silicon polymer tubing (0.025 in I.D., 0.047 in O.D., Dow Corning Corporation, Midland, Mich.), as described by Xu and Melethil (21). The tubing was then connected to an infusion pump (Harvard Apparatus Co., Inc., Millis, Mass.), and freshly made 0.9% NaCl, 5% glucose, arginine, GIP or GLP-1 (peptides and arginine dissolved in 0.9% NaCl) was infused at a rate of 0.1 ml/min. Blood (0.5 ml each) was obtained at 0, 10, 20, and 30 min by translumbar vena cava puncture, as described by Winsett et al. (1985, Am. J. Physiol., 249: G145–146), and samples were centrifuged at 2,000 g for 10 min. Serum samples were separated and stored at −20° C. until assayed for insulin using a radioimmunoassay kit (ICN Biochemicals, Costa Mesa, Calif.), and glucose, using a One Touch β glucose meter (Lifescan, INS., Milpitas, Calif.).

Figure 4:
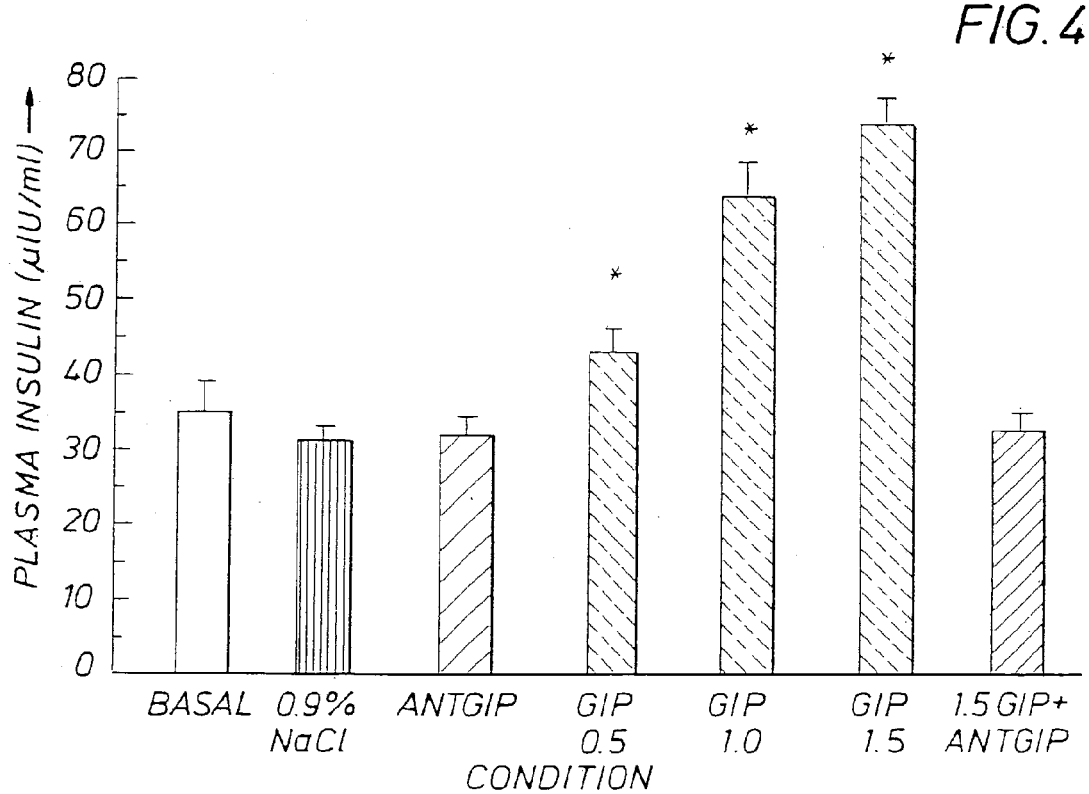
FIG. 4 shows plasma insulin concentrations (±SE) in fasted anesthetized rats after 30 min of GIP, ANTGIP (SEQ ID NO:8), or 0.9 NaCl infusion.

To examine the insulinotropic effect of GIP in vivo, fasted anesthetized rats were perfused continuously with three different concentrations of GIP (0.5, 1.0, and 1.5 nmol/kg) at a rate of 0.1 ml/min for 30 min ($10^{-8}$ M equivalent to 1 mmol/kg/30 min). Significant increases in plasma insulin levels were first detected at 15 min, and after completion of the GIP infusion, insulin levels were elevated with all three GIP concentrations (43.5±2.7, 61.6±4.2, and 72.4±3.5 μIU/ml, respectively) compared to control (32.2±3.3 μIU/m, p<0.05, FIG. 4). The concomitant administration of ANTGIP (SEQ ID NO:8) (100 nmol/kg) completely abolished the insulinotropic properties of GIP (1.5 nmol/kg), with plasma insulin returning to control values (FIG. 4). GIP was infused at 0.5, 1.0, and 1.5 nmol/kg, with the largest insulin stimulatory response seen with 1.5 nmol/kg. ANTGIP (SEQ ID NO:8) (100 nmol/kg) administered concomitantly with GIP 1.5 nmol/kg completely abolished its insulinotropic effect, whereas ANTGIP (SEQ ID NO:8) and 0.9% NaCl infusion had no effect on insulin secretion (n=6 for each group, *p<0.05, compared with basal levels).

Figure 5:
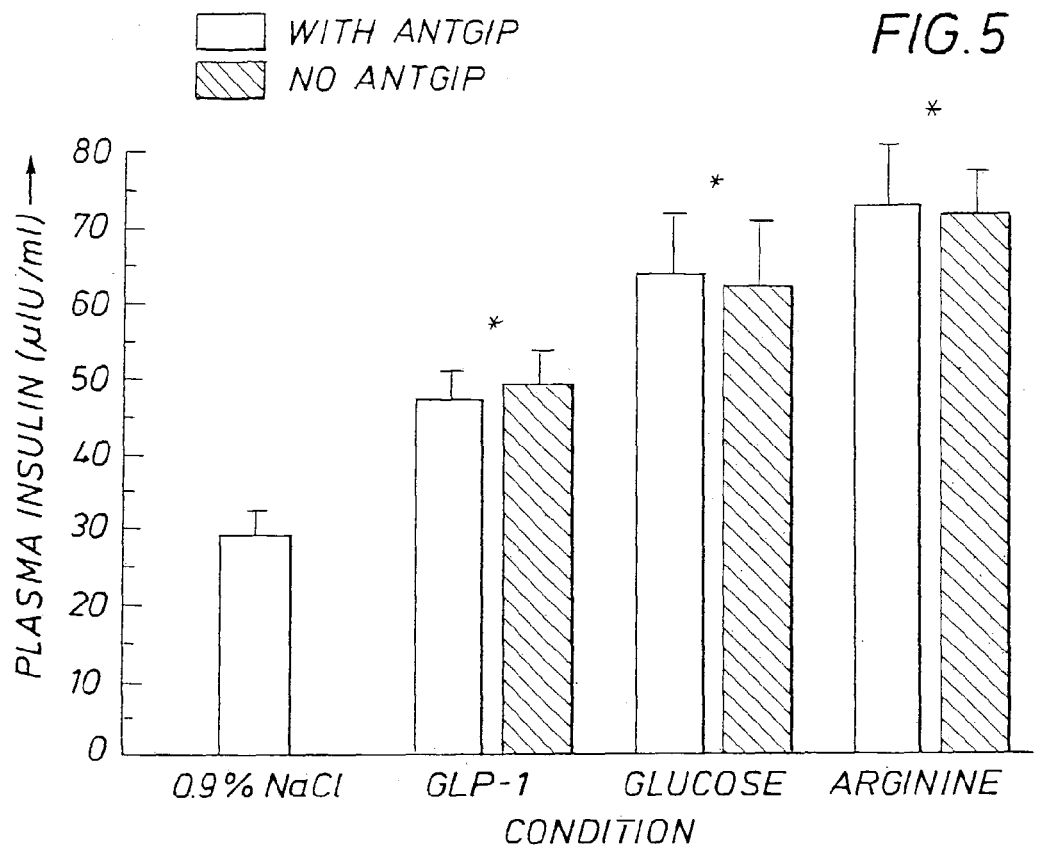
FIG. 5 shows plasma insulin concentrations (±SE) in fasted anesthetized rats after a 30-min infusion of GLP-1 (0.4 nmol/kg), glucose (0.8 g/kg), or arginine (375 mg/kg) with (open bars) or without (solid bars) ANTGIP (SEQ ID NO:8) (100 nmol/kg) (n=6 for each group).

To examine whether ANTGIP (SEQ ID NO:8) exerted a nonspecific effect on β-cell function, GLP-1 (0.4 nmol/kg), glucose (0.8 g/kg), or arginine (375 mg/kg) was infused, in the presence or absence of the antagonist for 30 min, as described by Wang et al. (13). FIG. 5 shows plasma insulin concentrations (±SE) in fasted anesthetized rats after a 30-min infusion of GLP-1 (0.4 nmol/kg), glucose (0.8 g/kg), or arginine (375 mg/kg) with (open bars) or without (solid bars) ANTGIP (SEQ ID NO:8) (100 nmol per kg) (n=6 for each group, *<0.05, compared with basal levels). GLP-1, glucose, and arginine alone each significantly increased insulin levels after 15 min of infusion, and by 30 min, the insulin levels in GLP-1-, glucose-, and arginine-infused rats were 50.3±3.7, 63.1±2.5, 69.7±5.8 μIU/ml respectively (p<0.01, compared with control rats, 29.1±2.9 μIU/ml, FIG. 5). No significant change in the insulin response was detected when ANTGIP (SEQ ID NO:8) was administered concomitantly (FIG. 5).

Example 4

Insulinotropic Effect of GIP in Trained Conscious Fed Rats

Postprandial plasma insulin and serum glucose levels were studied in conscious trained rats. Previous reports have indicated that the stress response to injection in untrained rats might alter their feeding and subsequently glucose and insulin levels (13). To avoid such a response, rats were trained for 10 d before experimentation. They were fasted from 17:00 to 08:00, and 0.9% NaCl (0.3 ml) was injected subcutaneously at 08:00 before feeding. After the injection of 0.9% NaCl, animals were given rat chow for 30 min, after which it was removed. At the end of ten days, the rats were accustomed to the injection and ate quickly (consuming 4–6 g of rat chow within 30 min).

On the day of the experiment, after fasting from 17:00 the night before, trained rats were injected subcutaneously at 08:00 with 0.3 ml of either 0.9% NaCl or ANTGIP (SEQ ID NO:8) (100 nmol/kg). This dose was chosen to approximately the amount of peptide used in the anesthetized animal studies of Example 3. After injection, six of the fasted control rats were killed to obtain baseline serum glucose and insulin levels. ANTGIP (SEQ ID NO:8)- or 0.9% NaCl-treated rats (n=6 in each group) were exposed to chow for 30 min, after which food was withdrawn. Rats were then anesthetized by intraperitoneal sodium penobarbital, and blood was collected by translumbar vena cava puncture at 20 and 40 min for the subsequent measurement of plasma insulin, glucose, and GLP-1.

Figure 6A:
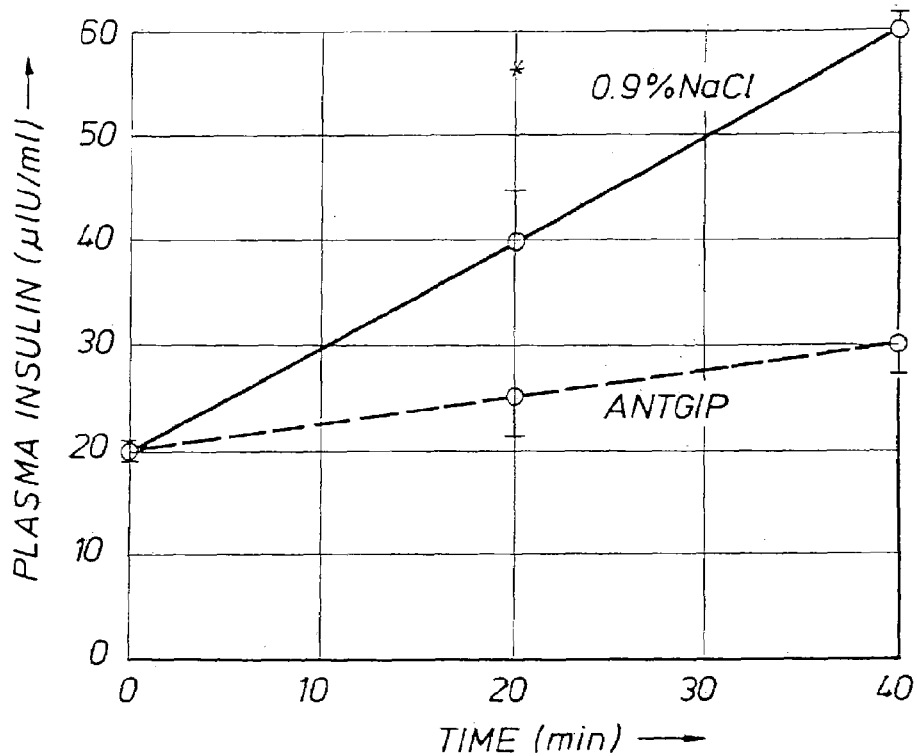
FIG. 6 shows postprandial plasma insulin and serum glucose levels (±SE) in conscious trained rats.
Figure 6B:
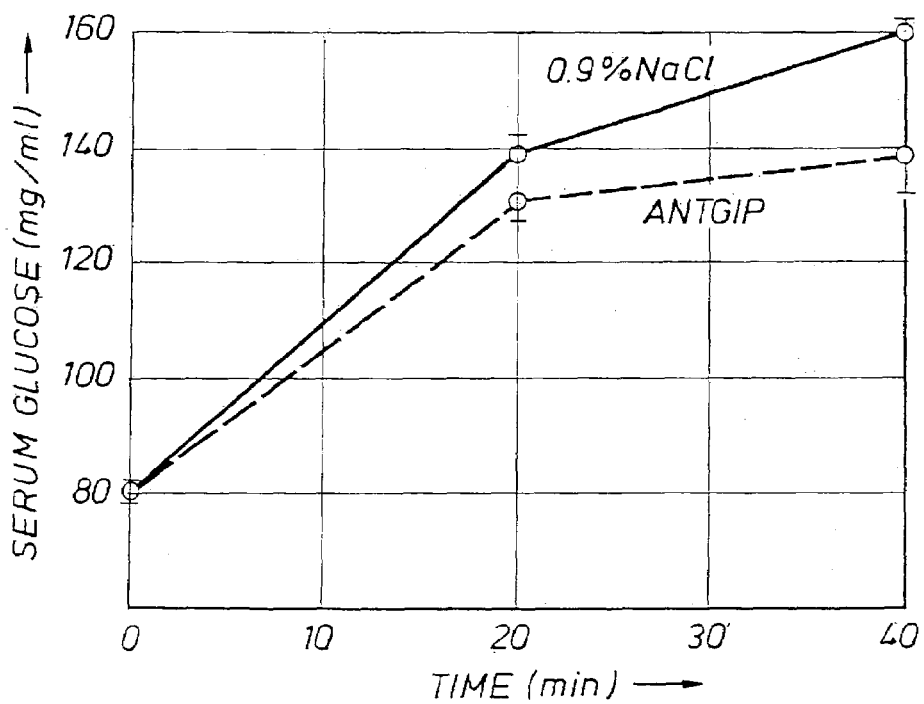

FIG. 6 shows postprandial plasma insulin and serum glucose levels (+SE) in conscious trained rats (*p<0.01 compared to ANTGIP (SEQ ID NO:8) injection). In response to consuming chow, serum glucose and plasma insulin levels increased significantly, with insulin levels of 38.7±5.3 and 58.9±3.7 μIU/ml at 20 and min, respectively (p<0.05, FIG. 6A). These increases in plasma insulin level were nearly abolished by ANTGIP (SEQ ID NO:8) pretreatment; at 20 and 40 min, the plasma insulin concentrations were 25.3±4.7 and 27.1±2.6 μIU/ml, respectively (p<0.01). Postprandial serum glucose concentrations were similar in both saline- and ANTGIP (SEQ ID NO:8)-treated rats (FIG. 6B). To determine whether the effects of the GIP receptor antagonist were mediated through changes in GLP-1 release into the circulation, postprandial serum GLP-1 levels were measured in both control and ANTGIP (SEQ ID NO:8)-treated animals. Meal stimulated serum GLP-1 concentrations were not affected by ANTGIP (SEQ ID NO:8) administration. Following the ingestion of rat chow, serum GLP-1 levels at 20 min were 280±20 and 290±10 pg/ml in control and ANTGIP (SEQ ID NO:8)-treated rats, respectively; at 40 min, serum GLP-I concentrations were 320±10 and 330±20 pg/mgl, respectively.

Example 5

Effect of ANTGIP (SEQ ID NO:8) on Glucose Tolerance and Plasma Insulin Levels Oral glucose tolerance tests were performed on rats injected intraperitoneally with ANTGIP (SEQ ID NO:8) (300 ng/kg) or 0.9% saline solution. After the intraperitoneal injection of 0.9% NaCl or ANTGIP (SEQ ID NO:8), an oral glucose tolerance test was performed. The test was done by administering a 40% glucose solution by oral gavage at a dose of 1 g per kg. The volume administered to each rat was approximately 0.5 ml. Blood was obtained at various time points for subsequent measurement of plasma insulin and glucose levels.

Figure 7:
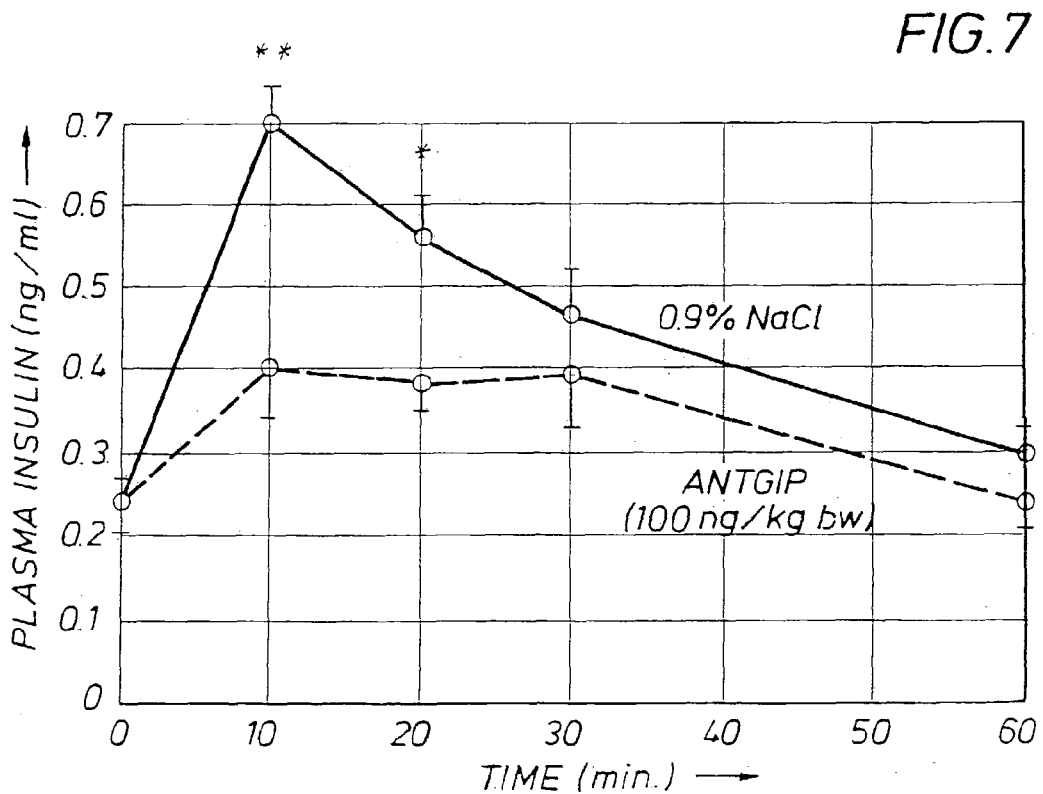
FIG. 7 shows plasma insulin level following oral glucose administration to rats with or without ANTGIP (SEQ ID NO:8) injection.
Figure 8:
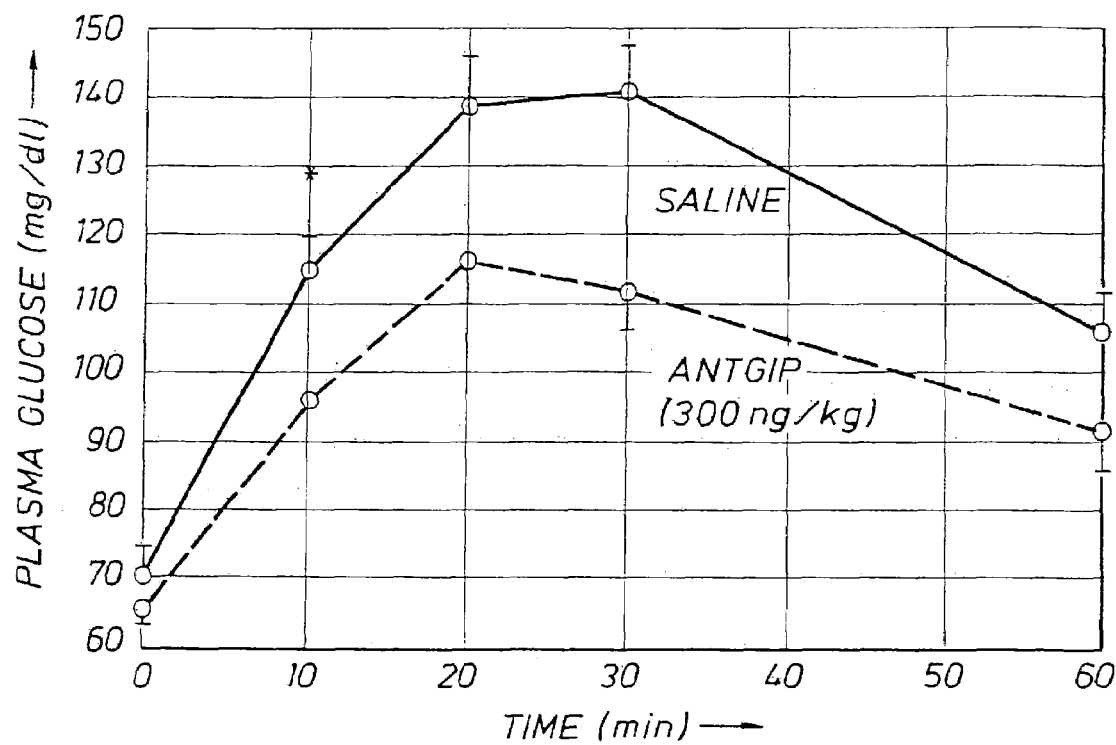
FIG. 8 shows plasma glucose level following oral glucose administration to rats with and without ANTGIP (SEQ ID NO:8) injection.

As expected in view of the experiment in Example 4, rats treated with ANTGIP (SEQ ID NO:8) showed reduced plasma insulin levels (FIG. 7). Surprisingly, plasma glucose was diminished at all time points in rats treated with ANTGIP (SEQ ID NO:8), compared to control rats (FIG. 8). Thus, ANTGIP (SEQ ID NO:8) increases or improves glucose tolerance, despite its negative effect on the insulinotropic response to GIP shown in Examples 3 and 4.

Example 6

Effect of GIP Receptor Antagonist on Intestinal Glucose Absorption

Male Sprague-Dawley rats weighing about 200–250 g are fasted overnight and anesthetized using intraperitoneal urethane (about 1.25 g per kg body weight). After midline laparotomy, an about 30-cm segment of jejunum, starting at about 5 cm distal to the ligament of Treitz, is isolated and flushed with approximately 20 ml of about 0.9% NaCl. The jejunal test segments are each perfused twice, initially with control buffer and then once again with control buffer or with the test solution. The test solution consists of Kres-Ringer-bicarbonate buffer containing about 5 mmol/L [$^{14}$C] D-glucose, and $^3$H-labeled polyethylene glycol is included in the luminal perfusate to correct for fluid movement. The test or control solution is perfused through the jejunal segment without recirculation at a flow rate of about 1.6 ml/min, using a Harvard PHD 2000 syringe pump (Harvard Apparatus, Millis, Mass.). The effluent from the luminal segment is collected at about 5-min intervals for about 30 min. After the initial period of perfusion, the luminal contents in the jejunum are flushed with about 20 ml of about 0.9% NaCl prior to the initiation of the second period of perfusion. In all experiments, animals are administered either about 0.9% NaCl (control) or ANTGIP (SEQ ID NO:8) (10 nmol/kg body weight) though the inferior vena cava by single injection at about time 0 min.

Figure 9:
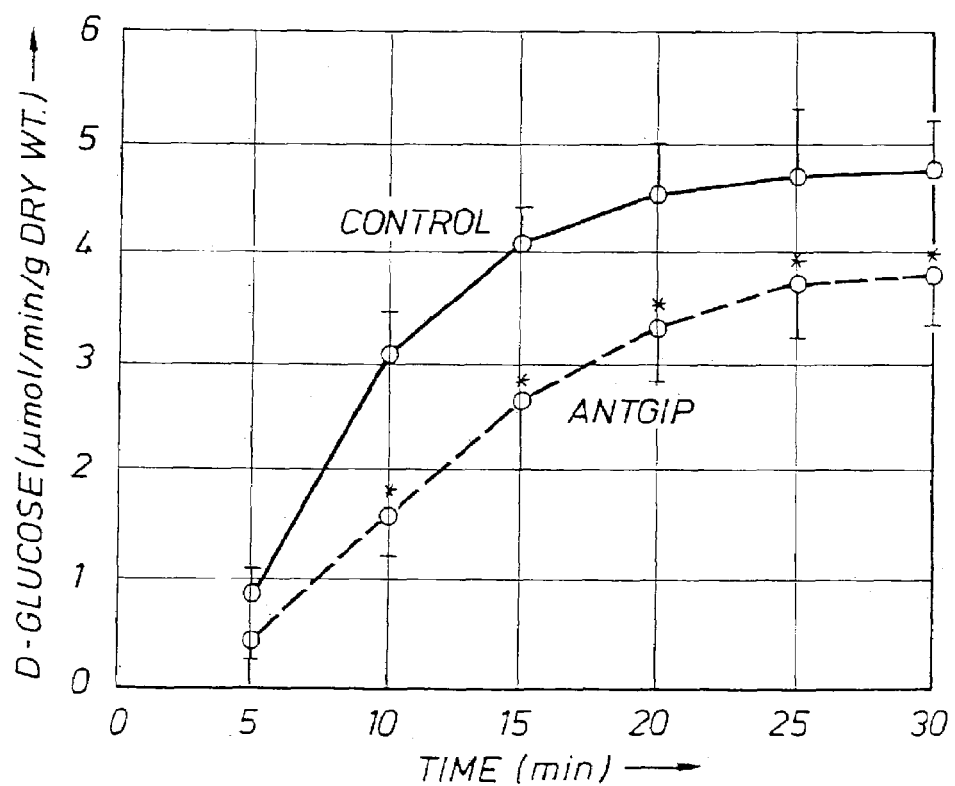
FIG. 9 shows the effects of the GIP receptor antagonist, ANTGIP (SEQ ID NO:8), on the absorption of free D-glucose from the lumen of the jejunal test segment.

The enclosed FIG. 9 depicts the effects of the GIP receptor antagonist, ANTGIP (SEQ ID NO:8), on the absorption of free D-glucose from the lumen of the jejunal test segment. Data points are believed to represent the rate of glucose disappearance from the luminal perfusate corrected for fluid movement. Results are expressed as the mean±SE of five experiments. Statistical significance (*) is assigned if P<0.05. As seen in the figure, a ANTGIP (SEQ ID NO:8) is believed to significantly reduce the absorption of D-glucose from the jejunal test segment throughout the entire 30 minute period of perfusion. Thus, it is believed that one of the mechanisms by which GIP receptor antagonism may improve glucose tolerance is by decreasing intestinal glucose absorption.

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in medicine, molecular biology, pharmacology, and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference in their entireties to the same extent as if each individual publication or patent application was specifically and individually indicated to be incorporated by reference.

We claim:

1. An isolated glucose dependent insulinotropic polypeptide (GIP) antagonist consisting of SEQ ID NO:5.

2. An isolated polypeptide consisting of SEQ ID NO:5 wherein His at position 9 replaced with Arg.

3. A composition comprising the isolated polypeptide of claim 1 or claim 2 in a pharmaceutically acceptable vehicle.

4. The composition of claim 3 further comprising an inert pharmaceutical excipient selected from the group consisting of sweetening, flavoring, coloring, dispersing, disintegrating, binding, granulating, suspending, wetting, preservative and demulcent agents.

5. The composition of claim 4 wherein the composition is lyophilized.

6. A method for antagonizing binding of glucose to glucose-dependent insulinotropic polypeptide (GIP) receptor, comprising contacting said receptor with the isolated polypeptide of claim 1 or the isolated polypeptide of claim 2.

7. The method of claim 6 wherein the isolated polypeptide of claim 1 or the isolated polypeptide of claim 2 is comprised within a pharmaceutically acceptable composition.

8. A composition comprising an isolated polypeptide consisting of SEQ ID NO: 5 and an isolated polypeptide consisting of SEQ ID NO: 5 wherein His at position 9 is replaced with Arg.

9. The composition of claim 8 further comprising an inert pharmaceutical excipient selected from the group consisting of sweetening, flavoring, coloring, and demulcent agents.

10. The composition of claim 9 wherein the composition is lyophilized.

* * * * *

SEQUENCE LISTING

```
<160> NUMBER OF SEQ ID NOS: 14

<210> SEQ ID NO 1
<211> LENGTH: 30
<212> TYPE: PRT
<213> ORGANISM: Homo sapiens

<400> SEQUENCE: 1

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 2
<211> LENGTH: 24
<212> TYPE: PRT
<213> ORGANISM: Homo sapiens
```

-continued

<400> SEQUENCE: 2

Ile Ser Asp Tyr Ser Ile Ala Met Asp Lys Ile His Gln Gln Asp Phe
1               5                   10                  15

Val Asn Trp Leu Leu Ala Gln Lys
            20

<210> SEQ ID NO 3
<211> LENGTH: 15
<212> TYPE: PRT
<213> ORGANISM: Homo sapiens

<400> SEQUENCE: 3

Lys Ile His Gln Gln Asp Phe Val Asn Trp Leu Leu Ala Gln Lys
1               5                   10                  15

<210> SEQ ID NO 4
<211> LENGTH: 9
<212> TYPE: PRT
<213> ORGANISM: Homo sapiens or Rattus norvegicus

<400> SEQUENCE: 4

Ile Ser Asp Tyr Ser Ile Ala Met Asp
1               5

<210> SEQ ID NO 5
<211> LENGTH: 21
<212> TYPE: PRT
<213> ORGANISM: Homo sapiens

<400> SEQUENCE: 5

Tyr Ser Ile Ala Met Asp Lys Ile His Gln Gln Asp Phe Val Asn Trp
1               5                   10                  15

Leu Leu Ala Gln Lys
            20

<210> SEQ ID NO 6
<211> LENGTH: 3
<212> TYPE: PRT
<213> ORGANISM: Homo sapiens or Rattus norvegicus

<400> SEQUENCE: 6

Ile Ser Asp
1

<210> SEQ ID NO 7
<211> LENGTH: 30
<212> TYPE: PRT
<213> ORGANISM: Rattus norvegicus

<400> SEQUENCE: 7

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys
            20                  25                  30

<210> SEQ ID NO 8
<211> LENGTH: 24
<212> TYPE: PRT
<213> ORGANISM: Rattus norvegicus

<400> SEQUENCE: 8

Ile Ser Asp Tyr Ser Ile Ala Met Asp Lys Ile Arg Gln Gln Asp Phe

-continued

```
                1               5                  10                 15
Val Asn Trp Leu Leu Ala Gln Lys
            20

<210> SEQ ID NO 9
<211> LENGTH: 15
<212> TYPE: PRT
<213> ORGANISM: Rattus norvegicus

<400> SEQUENCE: 9

Lys Ile Arg Gln Gln Asp Phe Val Asn Trp Leu Leu Ala Gln Lys
 1               5                  10                 15

<210> SEQ ID NO 10
<211> LENGTH: 21
<212> TYPE: PRT
<213> ORGANISM: Rattus norvegicus

<400> SEQUENCE: 10

Tyr Ser Ile Ala Met Asp Lys Ile Arg Gln Gln Asp Phe Val Asn Trp
 1               5                  10                 15

Leu Leu Ala Gln Lys
            20

<210> SEQ ID NO 11
<211> LENGTH: 42
<212> TYPE: PRT
<213> ORGANISM: Homo sapiens

<400> SEQUENCE: 11

Tyr Ala Glu Gly Thr Phe Ile Ser Asp Tyr Ser Ile Ala Met Asp Lys
 1               5                  10                 15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 12
<211> LENGTH: 42
<212> TYPE: PRT
<213> ORGANISM: Rattus norvegicus

<400> SEQUENCE: 12

Tyr Ala Glu Gly Thr Phe Ile Ser Asp Tyr Ser Ile Ala Met Asp Lys
 1               5                  10                 15

Ile Arg Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 13
<211> LENGTH: 10
<212> TYPE: PRT
<213> ORGANISM: Homo sapiens or Rattus norvegicus

<400> SEQUENCE: 13

Asp Phe Val Asn Trp Leu Leu Ala Gln Lys
 1               5                  10

<210> SEQ ID NO 14
<211> LENGTH: 14
<212> TYPE: PRT
```

-continued

```
<213> ORGANISM: Rattus norvegicus

<400> SEQUENCE: 14

Gly Lys Lys Asn Asp Trp Lys His Asn Leu Thr Gln Arg Glu
1               5                   10
```